United States Patent
Pfeiffer et al.

(10) Patent No.: US 9,668,754 B2
(45) Date of Patent: Jun. 6, 2017

(54) SYSTEM, APPARATUS, AND METHOD FOR GRAFTING TISSUE

(71) Applicants: Ferris M. Pfeiffer, Boonville, MO (US); Aaron M. Stoker, Columbia, MO (US); James L. Cook, Columbia, MO (US)

(72) Inventors: Ferris M. Pfeiffer, Boonville, MO (US); Aaron M. Stoker, Columbia, MO (US); James L. Cook, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 590 days.

(21) Appl. No.: 14/102,187

(22) Filed: Dec. 10, 2013

(65) Prior Publication Data

US 2014/0180414 A1 Jun. 26, 2014

Related U.S. Application Data

(60) Provisional application No. 61/735,456, filed on Dec. 10, 2012.

(51) Int. Cl.
*A61B 17/16* (2006.01)
*A61B 17/34* (2006.01)

(52) U.S. Cl.
CPC .......... *A61B 17/1635* (2013.01); *A61B 17/16* (2013.01); *A61B 17/1604* (2013.01); *A61B 17/1613* (2013.01); *A61B 17/1615* (2013.01); *A61B 17/3417* (2013.01); *A61B 17/3439* (2013.01)

(58) Field of Classification Search
CPC . A61B 17/16; A61B 17/1613; A61B 17/1615; A61B 17/1635; A61B 17/3417; A61B 17/3439; B23B 51/04; B23B 51/0406; B23B 51/0413; B23B 51/0453; B23B 51/05; B23B 2251/428; B23B 2251/54
See application file for complete search history.

(56) References Cited

U.S. PATENT DOCUMENTS

| | | | |
|---|---|---|---|
| 2,511,650 A | 6/1950 | Robinson | |
| 2003/0031521 A1 | 2/2003 | Haughton et al. | |
| 2005/0113836 A1* | 5/2005 | Lozier ................ | A61B 17/1617 606/80 |
| 2007/0233264 A1 | 10/2007 | Nycz et al. | |

FOREIGN PATENT DOCUMENTS

WO  WO 2009/057887  5/2009

OTHER PUBLICATIONS

International Search Report issued in PCT/US2013/074194, dated Mar. 6, 2014.

* cited by examiner

*Primary Examiner* — Larry E Waggle, Jr.
(74) *Attorney, Agent, or Firm* — Dentons US LLP

(57) ABSTRACT

Systems, apparatus, and methods may be adapted for grafting tissue at a tissue site that may include an elongate housing and a plurality of elongate cutting members. The plurality of elongate cutting members may define a cutting surface at a distal end of the elongate housing. The cutting surface may be adapted to contract from a first diameter to a second diameter that is less than the first diameter. The contraction of the cutting surface from the first diameter to the second diameter may define a tapered profile between the first diameter and the second diameter suitable for obtaining a tapered graft.

16 Claims, 10 Drawing Sheets

DAY 0, CYLINDRICAL

DAY 0, TAPERED

DAY 3, CYLINDRICAL

DAY 3, TAPERED

CYLINDRICAL GRAFT

TAPERED GRAFT

SYSTEM, APPARATUS, AND METHOD FOR GRAFTING TISSUE

RELATED APPLICATION

This application claims the benefit, under 35 USC §119(e), of U.S. Provisional Patent Application Ser. No. 61/735,456, entitled "System, Apparatus, and Method for Grafting Tissue," filed Dec. 10, 2012, which is incorporated herein by reference for all purposes.

BACKGROUND

1. Field

This specification relates generally to systems, apparatus, and methods adapted for grafting tissue at a tissue site. The systems, apparatus, and methods may be suitable, for example, for performing osteochondral allografts, autografts, and grafts with other tissue types.

2. Discussion

Common usages for tissue grafts may include the treatment of cartilage defects. For example, an osteochondral allograft (OCA) is a type of tissue graft commonly used to treat cartilage defects resulting from osteochondrosis, trauma, and osteoarthritis. Current OCA techniques may utilize cylindrically shaped grafts having a straight longitudinal sidewall that are inserted into a similarly shaped cylindrical cavity or socket and held in place with a press-fit interface. The insertion of the cylindrically shaped graft may require large insertion forces to overcome the frictional resistance between the sidewall of the cylindrical graft and a sidewall of the corresponding cylindrical cavity. Installation of the graft may require mechanical impacting. Studies have shown that such mechanical insertion techniques may negatively impact chondrocyte viability in the grafts and long term outcomes of the procedure.

SUMMARY

The disclosed systems, apparatus, and methods may be adapted, in part, to decrease insertion force and energy required to achieve installation of grafts to overcome the problems associated with conventional technologies and methods.

In some illustrative embodiments, a cutting apparatus for providing a tapered tissue graft may include an annular cutting surface that may be adapted to contract from a first diameter to a second diameter that is less than the first diameter.

In other illustrative embodiments, a cutting apparatus for providing a tapered tissue graft may include an elongate housing and a plurality of elongate cutting members. The elongate housing may have a proximal end, a distal end, and a bore defining a longitudinal axis. The elongate cutting members may define an annular cutting surface at the distal end of the elongate housing. The annular cutting surface may be adapted to contract from a first diameter to a second diameter that is less than the first diameter. The contraction of the annular cutting surface from the first diameter to the second diameter may define a tapered profile between the first diameter and the second diameter.

In some illustrative embodiments, a system adapted for grafting tissue at a tissue site, may include an elongate housing, a plurality of elongate cutting members, and a plunger. The elongate housing may have a proximal end, a distal end, and a bore defining a longitudinal axis. The plurality of elongate cutting members may extend lengthwise at the distal end of the elongate housing, and may be positioned about the longitudinal axis of the elongate housing. The elongate cutting members may define an annular cutting surface adapted to contract from a first diameter to a second diameter that is less than the first diameter. The contraction of the annular cutting surface from the first diameter to the second diameter may define a tapered profile between the first diameter and the second diameter. The plunger may have an external surface and may be slidably disposed in the bore of the elongate housing. When the annular cutting surface has the first diameter, the elongate cutting members may be biased against the external surface of the plunger at the distal end of the elongate housing.

In some illustrative embodiments, a method of grafting tissue at a tissue site may include inserting a tapered graft tissue into a corresponding tapered socket at the tissue site.

In other illustrative embodiments, a method of grafting tissue at a tissue site may include obtaining a tapered graft tissue having an insertion end and an exposed end separated by a length. The tapered graft tissue may have a first diameter at the exposed end that is larger than a second diameter at the insertion end. The length between the first diameter and the second diameter may define an external taper. The method may additionally include preparing a tapered socket in the tissue site for receiving the tapered graft tissue. The tapered socket may define an internal taper that substantially corresponds to the external taper of the tapered graft tissue. The method may also include inserting the tapered graft tissue into the tapered socket.

In other illustrative embodiments, a method of grafting tissue at a tissue site may include providing a cutting apparatus comprising an elongate housing, a plurality of elongate cutting members, and a plunger. The elongate housing may have a proximal end, a distal end, and a bore defining a longitudinal axis. The plurality of elongate cutting members may extend lengthwise at the distal end of the elongate housing, and may be positioned about the longitudinal axis of the elongate housing. The elongate cutting members may define an annular cutting surface that may be adapted to contract from a first diameter to a second diameter that is less than the first diameter. The contraction of the annular cutting surface from the first diameter to the second diameter may define a tapered profile between the first diameter and the second diameter. The plunger may have an external surface, and may be slidably disposed in the bore of the elongate housing. When the annular cutting surface has the first diameter, the elongate cutting members may be biased against the external surface of the plunger at the distal end of the elongate housing. The method may additionally include positioning the plunger at the distal end of the elongate housing to place the annular cutting surface in the first diameter, and inserting the annular cutting surface longitudinally into a donor tissue source. Further, the method may include displacing the plunger toward the proximal end of the elongate housing with donor tissue entering the bore of the elongate housing as the annular cutting surface advances into the donor tissue source. Additionally, the method may include obtaining a tapered graft tissue having an external taper by contracting the annular cutting surface from the first diameter to the second diameter along the tapered profile as the plunger is displaced. Further, the method may include reaming a tapered socket in the tissue site for receiving the tapered graft tissue. The tapered socket may define an internal taper that substantially corresponds to the external taper of the tapered graft tissue. The method may also include inserting the tapered graft tissue into the tapered socket.

In some illustrative embodiments, provided is a tapered graft tissue for inserting in a tapered socket. The tapered graft tissue may include an insertion end and an exposed end separated by a length. The tapered graft tissue may have a first diameter at the exposed end that is larger than a second diameter at the insertion end. The length between the first diameter and the second diameter may define an external taper.

Other objects, features, and advantages of the illustrative embodiments will become apparent with reference to the drawings and detailed description that follow.

DETAILED DESCRIPTION

Figure 1A:
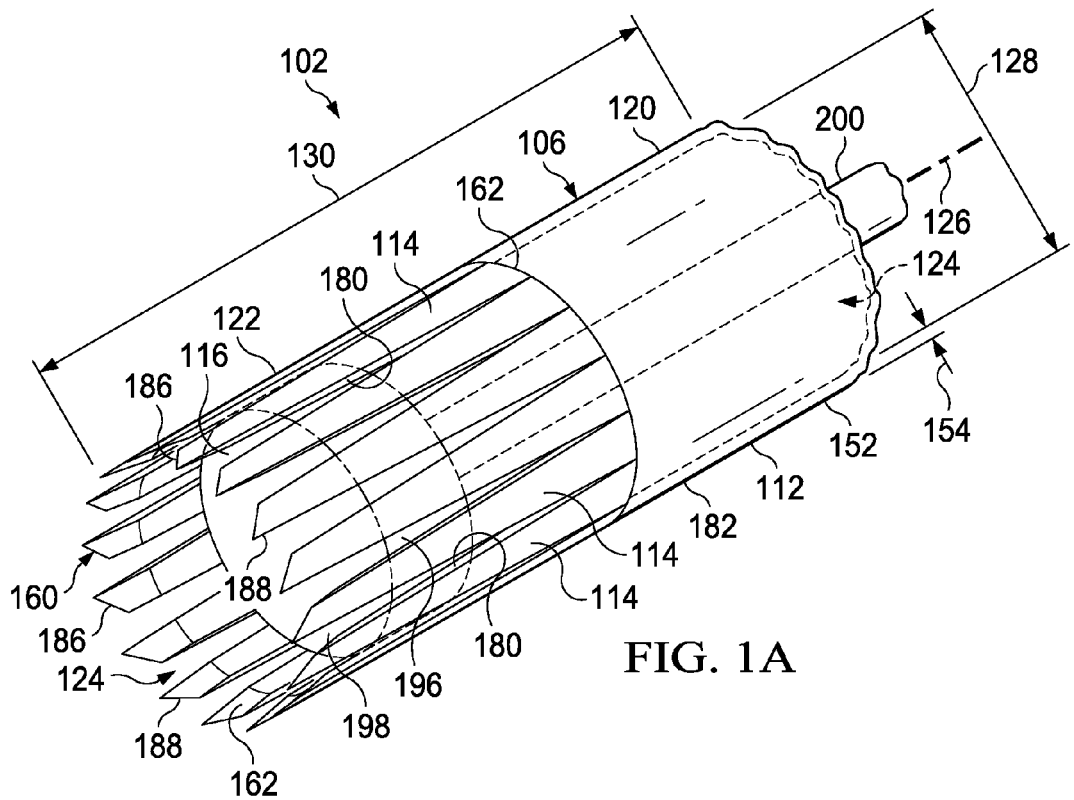
FIG. 1A is a perspective view of an illustrative embodiment of a cutting apparatus for grafting tissue at a tissue site depicting a plunger positioned toward a distal end of an elongate housing and an annular cutting surface positioned in a first diameter.

In the following detailed description, reference is made to the accompanying drawings that depict non-limiting illustrative embodiments for practicing the subject matter disclosed in this specification. Other embodiments may be utilized and logical, structural, mechanical, electrical, and chemical changes may be made without departing from the scope of this specification. To avoid detail not necessary to enable those skilled in the art to practice the subject matter disclosed herein, the description may omit certain information known to those skilled in the art. Therefore, the following detailed description is provided without limitation, and with the scope of the illustrative embodiments being defined by the appended claims.

This specification relates to systems, apparatus, and methods that may be adapted to provide a tissue graft having a tapered external surface and a corresponding internally tapered socket in a tissue site for receiving the tissue graft. The disclosed systems, apparatus, and methods may reduce the forces required to implant the tapered tissue graft in the tapered socket while attaining the desired stability for graft healing and incorporation. The benefits may include increased chondrocyte viability and an increase in likelihood of success for the grafting procedure.

Referring to FIGS. 1-6, provided is a system 102 that may be adapted for grafting tissue at a tissue site 104. The system 102 may comprise a cutting apparatus 106 for cutting a tapered graft tissue 108. The cutting apparatus 106 may include an elongate housing 112 and a plurality of elongate cutting members 114. The cutting apparatus 106 may additionally include a plunger 116 that may be adapted to actuate the elongate cutting members 114 as described below.

Referring to FIGS. 1A-4, the elongate housing 112 may have a proximal end 120, a distal end 122, and a bore 124 defining a longitudinal axis 126. The bore 124 of the elongate housing 112 may have a substantially constant internal diameter 128 along a length 130 of the elongate housing 112. The elongate housing 112 may include optional features, such as, for example, grasping handles 134 and an arbor 136. The grasping handles 134 may be positioned near the proximal end 120 of the elongate housing 112 to provide stability during operation. The arbor 136 may be adapted, without limitation, to facilitate operation of the system 102 in combination with a desired surgical implement. The operation of the system 102 will be described in further detail below.

Figure 2:
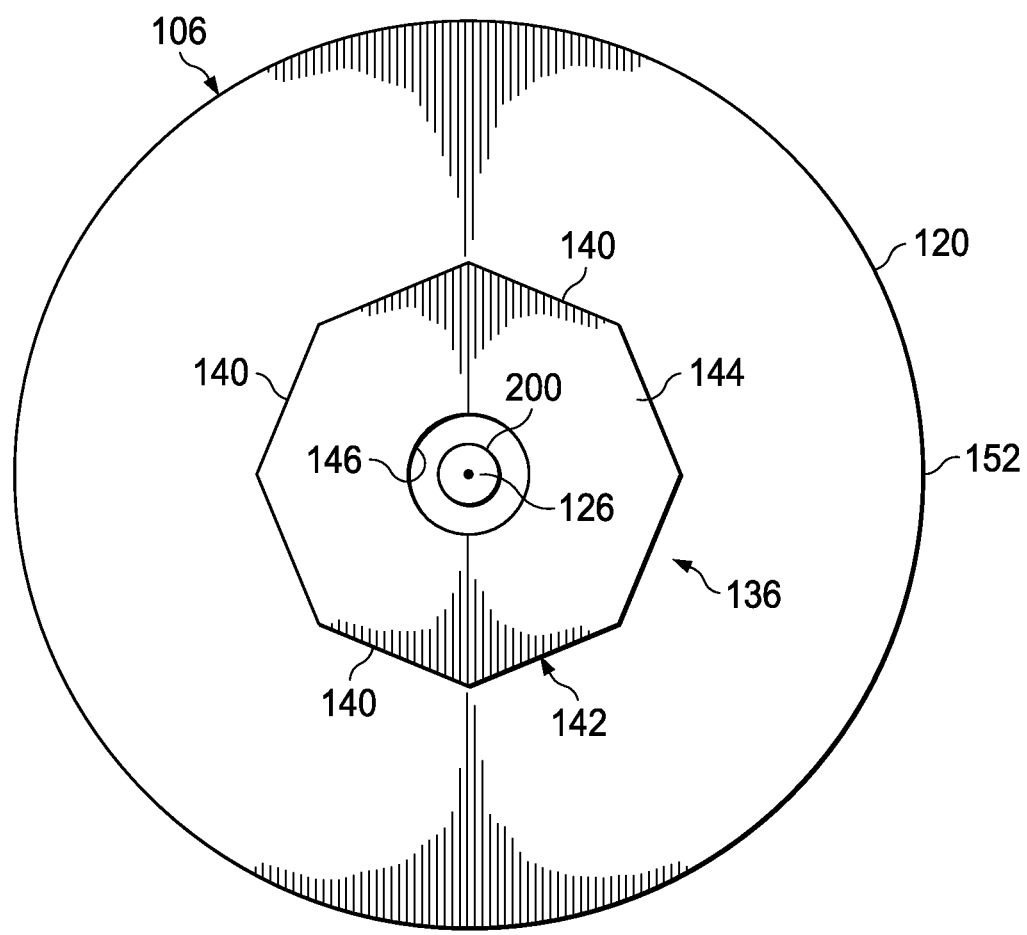
FIG. 2 is a top view of a proximal end of an illustrative embodiment of a cutting apparatus for grafting tissue at a tissue site, depicting a plunger guide rod received within an arbor coupled to an elongate housing.
Figure 3:
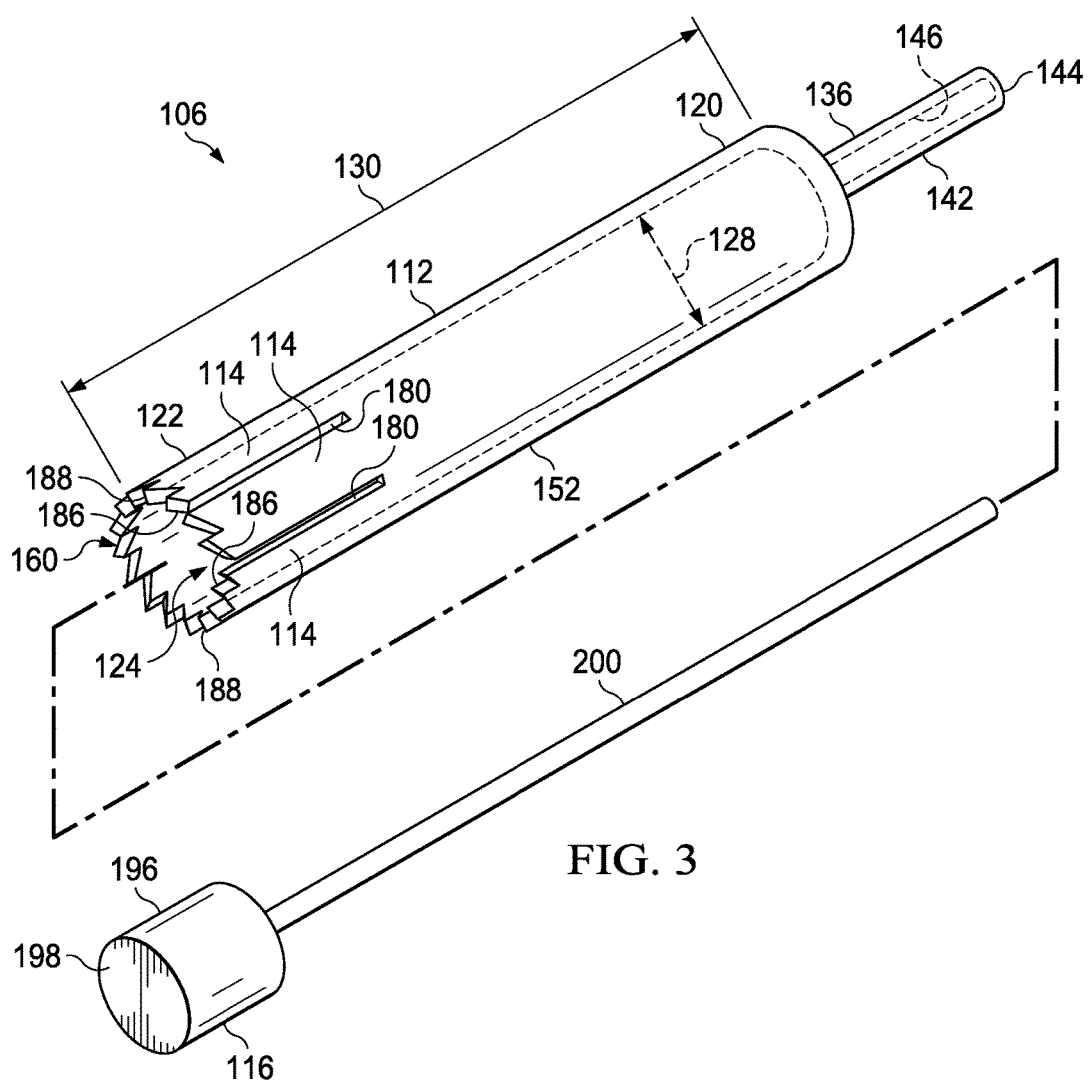
FIG. 3 is a perspective view of an illustrative embodiment of a cutting apparatus for grafting tissue at a tissue site including an annular cutting surface having serrations.
Figure 4:
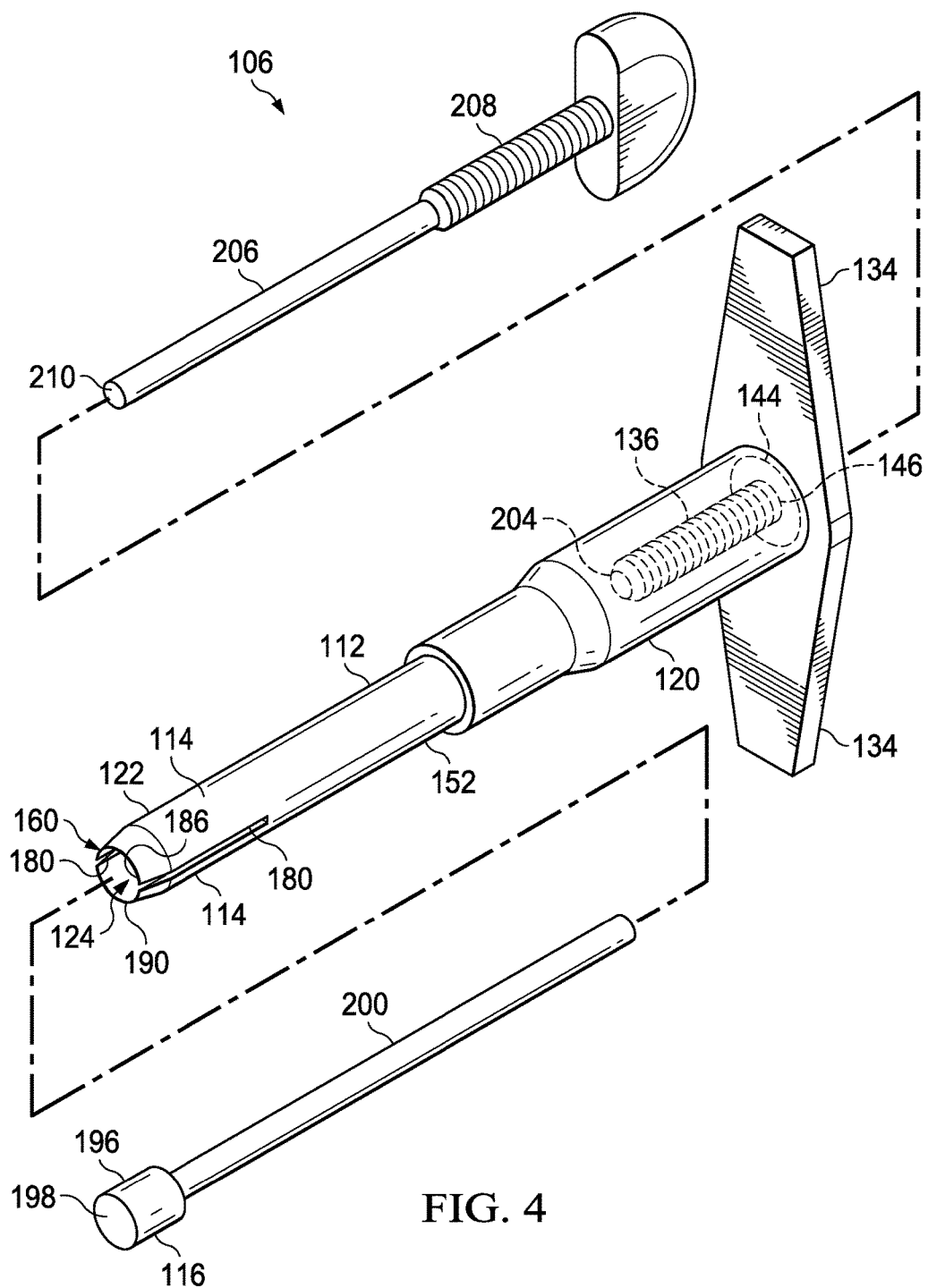
FIG. 4 is a perspective view of an illustrative embodiment of a cutting apparatus for grafting tissue at a tissue site including a smooth annular cutting surface.

The arbor 136 may be positioned at the proximal end 120 of the elongate housing 112 and may be substantially aligned with the longitudinal axis 126 of the elongate housing 112. For example, the arbor 136 may be substantially concentric to the longitudinal axis 126 and the bore 124 of the elongate housing 112. In some embodiments, as depicted in FIGS. 2-3, the arbor 136 may be adapted to couple the elongate housing 112 to a surgical implement, such as a drill. For example, the arbor 136 may have an octagonal cross-section or other shape having flat surfaces 140 or keyways disposed about a circumferential surface 142 or perimeter of the arbor 136, to provide grip for the surgical implement. The arbor 136 may also provide an impact surface 144 at the proximal end 120 of the elongate housing 112 adapted to receive blows from, for example, a hammer or similar instrument. In some embodiments, as depicted in FIG. 4, the impact surface 144 of the arbor 136 may be a portion of increased surface area on the proximal end 120 of the elongate housing 112. In other embodiments, the impact surface 144 may be separate from the arbor 136. The arbor 136 may include an aperture 146 that may be substantially aligned with or concentric to the longitudinal axis 126 of the elongate housing 112 for use in guiding the plunger 116 as described below.

Continuing with FIGS. 1A-4, the elongate housing 112 may have a circular cross section, and may be, for example, a tube formed of stainless steel, titanium, or similar material. The internal diameter 128 or dimension of the bore 124 of the elongate housing 112 may be, for example, between about 3 millimeters to about 30 millimeters. Further, the elongate housing 112 may have a wall 152 with a wall thickness 154 of about 1 millimeter or less. However, the elongate housing 112 is not limited to any particular internal diameter 128 or dimension, or wall thickness 154. Further, the arbor 136 may be formed integrally with the elongate housing 112 or as a separate component that may be coupled to the elongate housing 112. Without limitation, the arbor 136 may be formed of similar materials described above for the elongate housing 112.

Referring to FIGS. 1A-1B, 3-4, and 6, the plurality of elongate cutting members 114 may extend lengthwise at the distal end 122 of the elongate housing 112 and may be positioned about the longitudinal axis 126 of the elongate housing 112. The elongate cutting members 114 may define a substantially annular cutting surface 160 that may be adapted to contract from a first diameter 162 or first dimension shown in FIG. 1A to a second diameter 164 or second dimension shown in FIG. 1B. The second diameter 164 or dimension may be less than the first diameter 162 or dimension. Further, the first diameter 162 or dimension may be substantially concentric to the second diameter 164 or dimension, and the first diameter 162 or dimension may substantially correspond to the internal diameter 128 of the elongate housing 112. The contraction of the annular cutting surface 160 from the first diameter 162 or dimension to the second diameter 164 or dimension may define a tapered profile 168 between the first diameter 162 or dimension and the second diameter 164 or dimension. The tapered profile 168 may have any dimensions and rate of taper suitable for a particular grafting procedure. As described below, the tapered profile 168 between the first diameter 162 or dimension and the second diameter 164 or dimension of the annular cutting surface 160 may provide the tapered graft tissue 108 with an external taper 172 or tapered sidewall. The external taper 172 or tapered sidewall of the tapered graft tissue 108 may substantially correspond to the tapered profile 168 of the annular cutting surface 160 along an entire length 174 of the tapered graft tissue 108. Although FIGS. 1A-1B and 3-4 illustrate the annular cutting surface 160 as being substantially annular or circular in shape, other shapes are possible.

Figure 1B:
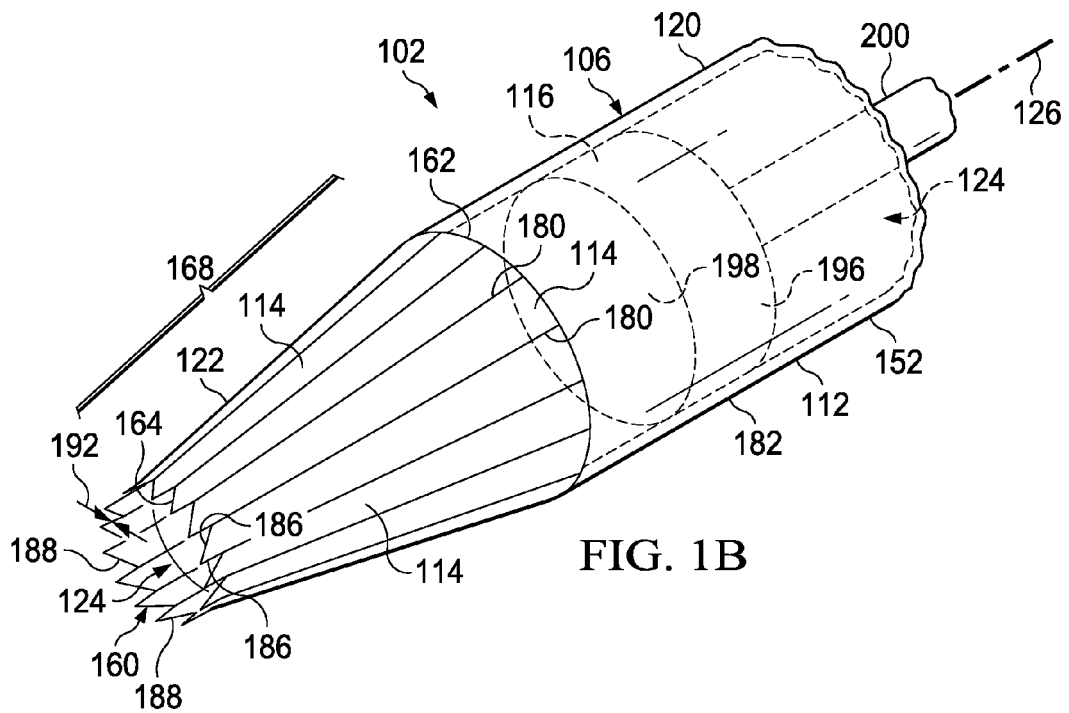
FIG. 1B is a perspective view of the cutting apparatus of FIG. 1A, depicting the plunger positioned toward a proximal end of the elongate housing and the annular cutting surface positioned in a second diameter.

Continuing with FIGS. 1A-1B and 3-4, the elongate cutting members 114 may be formed, for example, integrally with the elongate housing 112 or as separate components coupled to the elongate housing 112. In some embodiments, the elongate housing 112 may have longitudinal cuts 180 through the wall 152 of the elongate housing 112 that provide the elongate cutting members 114. The longitudinal cuts 180 may extend lengthwise along a portion of the distal end 122 of the elongate housing 112 and about a circumference 182 or perimeter of the elongate housing 112. In this manner, the longitudinal cuts 180 may provide the elongate cutting members 114 substantially as individual spring-like fingers at the distal end 122 of the elongate housing 112. Each of the elongate cutting members 114 or spring-like fingers may have at least one cutting tip 186. In a relaxed state as shown in FIG. 1B, the elongate cutting members 114 may be spring biased inward toward the bore 124 of the elongate housing 112, positioning the annular cutting surface 160 in the second diameter 164. Further, the longitudinal cuts 180 may be pie-shaped as shown in FIG. 1A to permit clearance between each of the elongate cutting members 114 when the annular cutting surface 160 is in the relaxed state and positioned in the second diameter 164.

The at least one cutting tip 186 associated with each of the elongate cutting members 114 may have any shape suitable for a particular application. For example, FIGS. 1A-1B depict an embodiment that may have one pointed cutting tip 188 positioned at an end of each of the elongate cutting members 114. FIG. 3 depicts an embodiment that may have a plurality of pointed cutting tips 188 positioned at an end of each of the elongate cutting members 114 to provide saw-like serrations. FIG. 4 depicts an embodiment that may have one flat cutting tip 190 positioned at an end of each of the elongate cutting members 114. The flat cutting tip 190 may be smooth rather than pointed or serrated as shown in FIGS. 1A-1B and 3, respectively.

Similar to the elongate housing 112, the first diameter 162 or dimension of the annular cutting surface 160 may be, for example, between about 3 millimeters to about 30 millimeters. The second diameter 164 or dimension of the annular cutting surface 160 may be any suitable diameter that is less than the first diameter 162. Further, the annular cutting surface 160 may have a thickness 192 of about 1.0 millimeter or less. However, the annular cutting surface 160 is not limited to any particular diameter or dimension, or thickness. Without limitation, the elongate cutting members 114 may be formed of similar materials described above for the elongate housing 112.

Referring to FIGS. 1A-4, the plunger 116 may have an external surface 196 and a tissue contact surface 198 and may be slidably disposed in the bore 124 of the elongate housing 112. The plunger 116 may include a plunger guide rod 200 that may be adapted to extend from the plunger 116 along the longitudinal axis 126 of the elongate housing 112. If the elongate housing 112 includes the optional arbor 136, in some embodiments, the aperture 146 in the arbor 136 may receive the plunger guide rod 200 to assist with guiding the plunger 116 in the bore 124 of the elongate housing 112. Further, the plunger guide rod 200 may protrude through the aperture 146 in the arbor 136 to the exterior of the elongate housing 112 to permit an operator to actuate the plunger 116 from the exterior of the elongate housing 112.

In some embodiments, as shown in FIG. 4, the aperture 146 in the arbor 136 may have internal threads 204 sized to receive an actuation rod 206 having a corresponding externally threaded surface 208 and an end 210 adapted to extend from the arbor 136 into the bore 124 of the elongate housing 112. The end 210 of the actuation rod 206 may engage the plunger guide rod 200 in the bore 124 of the elongate housing 112 for actuating the plunger 116 from the exterior of the elongate housing 112 as the actuation rod 206 moves along the internal threads 204 of the arbor 136.

Figure 11:
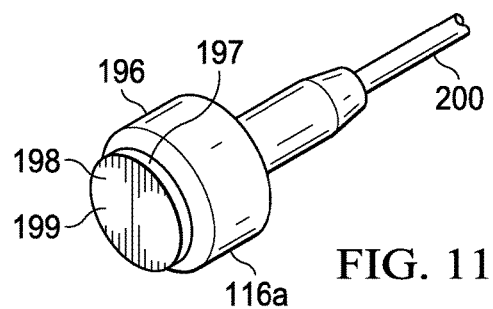
FIG. 11 provides an illustrative embodiment of a plunger that may include an external surface rotatable about a tissue contact surface.

Referring to FIG. 11, in some illustrative embodiments, the plunger 116 may be a plunger 116a including a bearing (not shown) that may permit the external surface 196 of the plunger 116a to rotate about or relative to the tissue contact surface 198 of the plunger 116a. In the embodiment of FIG. 11, the tissue contact surface 198 may be a button 199 that is rotatable on the bearing relative to the external surface 196. In this manner, the tissue contact surface 198, or the button 199, may be substantially precluded from rotating relative to the tapered graft tissue 108 during operation, permitting the tissue contact surface 198, or the button 199, to remain substantially stationary relative to the tapered graft tissue 108. For example, a circumference 197 of the tissue contact surface 198, or the button 199, may carry a bearing race (not shown) with the external surface 196 of the plunger 116a being disposed about the bearing race and rotatable thereabout. Utilizing the bearing with the plunger 116a may enhance the ability of the plunger 116a and cutting apparatus 106 to avoid damage to the tapered graft tissue 108.

Continuing with FIGS. 1A-4, when the annular cutting surface 160 has the first diameter 162 as shown in FIG. 1A, the elongate cutting members 114 may be biased against the external surface 196 of the plunger 116 at the distal end 122 of the elongate housing 112. When the plunger 116 is positioned at the distal end 122 of the elongate housing 112, the elongate cutting members 114 may be moved away from the relaxed state against a spring bias to position the annular cutting surface 160 in the first diameter 162. As shown in FIG. 1B, the plunger 116 may be slidable toward the proximal end 120 of the elongate housing 112 to permit the annular cutting surface 160 to gradually contract to the second diameter 164 and return to the relaxed state. In this manner, as described further below, the annular cutting surface 160 may be adapted to automatically contract from the first diameter 162 in FIG. 1A to the second diameter 164 in FIG. 1B as the annular cutting surface 160 advances into an object and the object enters the bore 124 of the elongate housing 112, displacing the plunger 116 toward the proximal end 120.

The plunger 116 and the plunger guide rod 200 may be formed integrally or as separate components coupled to one another. Further, the plunger 116 and the plunger guide rod 200 may be formed of any suitable material, such as, for example, stainless steel, titanium, or other suitable material. The external surface 196 of the plunger 116 may have any suitable size capable of fitting within the bore 124 of the elongate housing 112 and moving the elongate cutting members 114 to position the annular cutting surface 160 in the first diameter 162. For example, an increase in the external diameter of the plunger 116 may correspond to an increase in the first diameter 162 of the annular cutting surface 160.

Figure 5A:
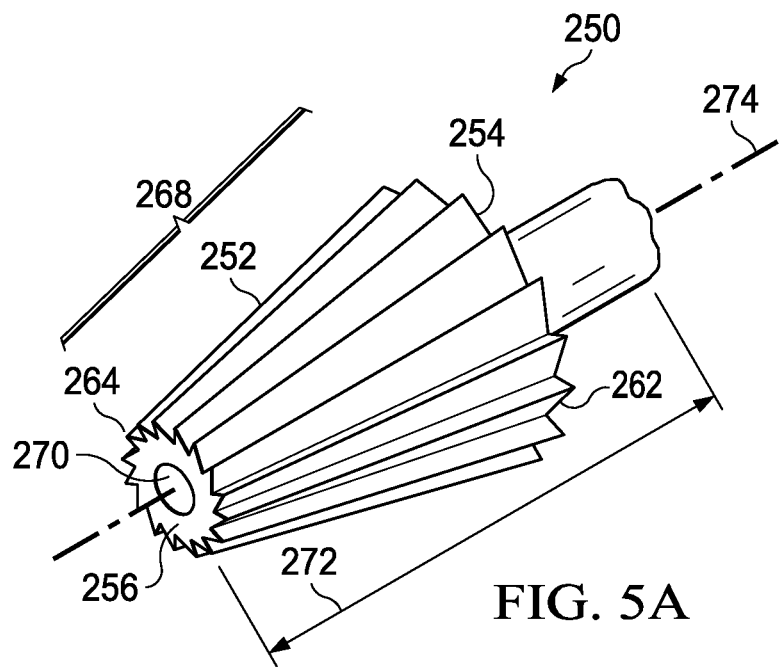
FIG. 5A is a perspective view of an illustrative embodiment of a tapered reamer.
Figure 5B:
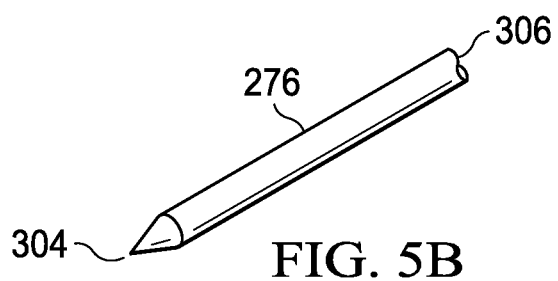
FIG. 5B is a perspective view of a reamer guide pin suitable for use with the tapered reamer of FIG. 5A.

Referring to FIGS. 5A-5B, the system 102 may include a reamer 250 that may have an external cutting surface 252, a proximal end 254, and a distal end 256. The external cutting surface 252 of the reamer 250 may have a first diameter 262 or proximal diameter at the proximal end 254 of the reamer 250 and a second diameter 264 or distal diameter at the distal end 256 of the reamer 250. The first diameter 262 at the proximal end 254 of the reamer 250 may be larger than the second diameter 264 at the distal end 256 of the reamer 250. The reamer 250 may be a tapered reamer and may define a tapered profile 268, or reamer taper, between the first diameter 262 and the second diameter 264 of the reamer 250. The tapered profile 268 between the first diameter 262 and the second diameter 264 of the reamer 250 may substantially correspond to the tapered profile 168 between the first diameter 162 and the second diameter 164 of the annular cutting surface 160. The reamer 250 may have a reamer bore 270 or guide bore substantially aligned along a length 272 and about a longitudinal axis 274 of the reamer 250 that may be adapted to receive a reamer guide pin 276. The reamer 250 may be rotatable about the reamer guide pin 276. The reamer 250 and the reamer guide pin 276 may be formed of any suitable material, such as, for example, stainless steel or titanium.

Referring generally to FIGS. 1-6, in an illustrative embodiment of operation, an operator may position the plunger 116 at the distal end 122 of the elongate housing 112 to position the annular cutting surface 160 in the first diameter 162 as shown in FIG. 1A. Upon positioning the plunger 116 and the annular cutting surface 160 in the first diameter 162, the operator may insert the annular cutting surface 160 longitudinally into a donor tissue source (not shown). The annular cutting surface 160 may be advanced into the donor tissue source along the longitudinal axis 126 of the elongate housing 112 by pressing the annular cutting surface 160 into the donor tissue source with or without rotation of the annular cutting surface 160. Lubrication such as saline may be applied to the plunger 116 and annular cutting surface 160 prior to and during insertion into the donor tissue source. Upon insertion into the donor tissue source, the plunger 116 may move toward the proximal end 120 of the elongate housing 112 and be displaced by donor tissue entering the bore 124 of the elongate housing 112 as the annular cutting surface 160 proceeds into the donor tissue source. The operator may obtain the tapered graft tissue 108 having the external taper 172 by the contracting action of the annular cutting surface 160 from the first diameter 162 to the second diameter 164 along the tapered profile 168 as the plunger 116 is displaced toward the proximal end 120 of the elongate housing 112. The tapered graft tissue 108 may be captured within the bore 124 of the elongate housing 112 when the annular cutting surface 160 contracts to the second diameter 164. The tapered graft tissue 108 may be extracted from the bore 124 of the elongate housing 112 by returning the plunger 116 from the proximal end 120 of the elongate housing 112 to the distal end 122 of the elongate housing 112. In some embodiments, the tapered graft tissue 108 may be extracted from an opening (not shown) at the proximal end 120 of the elongate housing 112.

Figure 6:
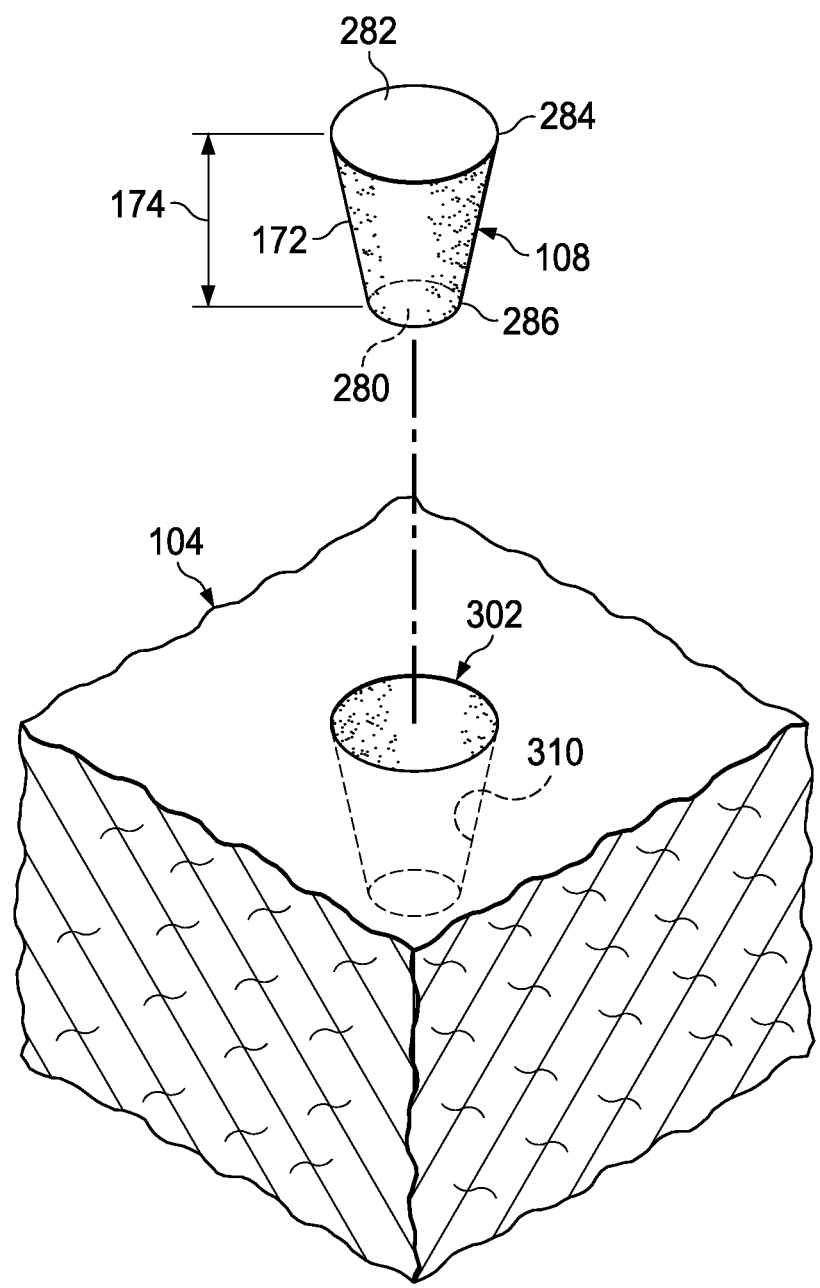
FIG. 6 is a perspective view of a an illustrative embodiment of a tapered graft tissue and an illustrative embodiment of a corresponding tapered socket in a tissue site.

Referring to FIG. 6, the tapered graft tissue 108 may include a graft insertion end 280 and a graft exposed end 282 separated by the length 174 of the tapered graft tissue 108. The tapered graft tissue 108 may have a first diameter 284, or exposed end diameter, at the graft exposed end 282 that is larger than a second diameter 286, or insertion end diameter, at the graft insertion end 280. In some embodiments, substantially the entire length 174 between the first diameter 284 and the second diameter 286 of the tapered graft tissue 108 may define the external taper 172 of the tapered graft tissue 108.

Referring to FIGS. 5A-6, the reamer 250 may be used for reaming or preparing a tapered socket 302 in the tissue site 104 for receiving the tapered graft tissue 108. A pin insertion end 304 of the reamer guide pin 276 may be inserted into the tissue site 104 for adapting the tissue site 104 to receive the tapered graft 108. A pin exposed end 306, or opposite end of the reamer guide pin 276 that opposes the pin insertion end 304, may be inserted into the reamer bore 270 of the reamer 250. The reamer 250 may be rotated about the reamer guide pin 276 and advanced into the tissue site 104 while being guided longitudinally along the longitudinal axis 274 of the reamer 250 into the tissue site 104 by the reamer guide pin 276. Advancing the reamer 250 into the tissue site 104 with the distal end 256 of the reamer 250 facing the tissue site 104 may create the tapered socket 302 as shown in FIG. 6.

The tapered socket 302 may define an internal taper 310 that substantially corresponds to the external taper 172 of the tapered graft tissue 108 for receiving the tapered graft tissue 108 therein. Thus, the tapered graft tissue 108 may be adapted to self-align with the tapered socket 302 when the graft insertion end 280 of the tapered graft tissue 108 faces the tissue site 104 for insertion into the tapered socket 302. Further, the tapered graft tissue 108 and the tapered socket 302 may each have, for example, a conical, frustoconical, or pyramidal shape. After reaming or providing the tapered socket 302 in the tissue site 104, insertion of the tapered graft tissue 108 into the tapered socket 302 may take place. Prior to inserting the tapered graft tissue 108 into the tapered socket 302, the tapered socket 302 may be finish sized to receive the tapered graft tissue 108 with, for example, a tamp (not shown). The tamp may have an externally tapered profile substantially corresponding to the external taper 172 of the tapered graft tissue 108 to provide final sizing of the tapered socket 302 for accepting the tapered graft tissue 108.

Experimental Results

Figure 7A:
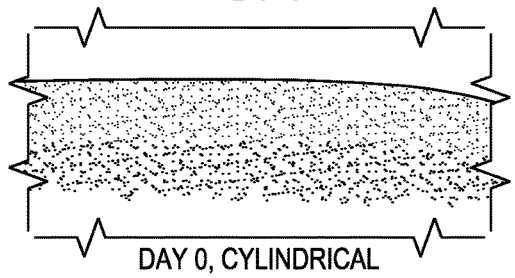
FIGS. 7A-7E illustrate experimental results of cell viability representative on day zero and day three for both a prior art cylindrical graft and a tapered graft tissue according to this disclosure.
Figure 7B:
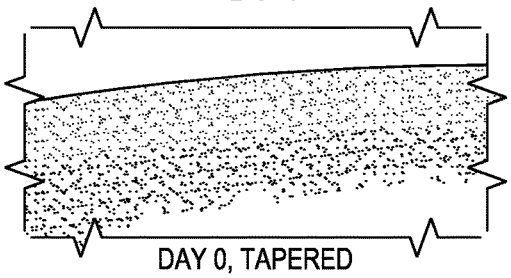
Figure 7C:
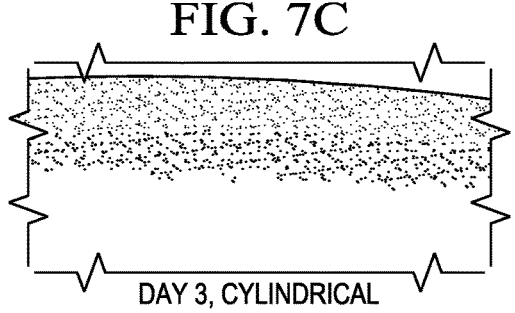
Figure 7D:
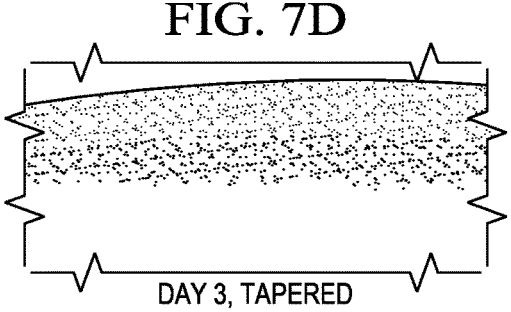

Referring to FIGS. 7A-9C, fresh femoral condyles and humeral heads were obtained from donor tissue sources. Cylindrical grafts 8 millimeters in diameter and 6 millimeters in height were created and implanted using a conventional system. Tapered grafts having an 8 millimeter first diameter at a top or exterior facing surface and a 6 millimeter height were implanted using a tapered graft system according to this disclosure. The cylindrical grafts and the tapered grafts were obtained from and implanted into the same specimen. After surgical implantation, the cylindrical grafts and the tapered grafts were analyzed at day zero to determine the immediate effect of graft implantation on cell viability and at day three to determine how changes in cell viability develop over time after implantation. For day zero testing, the cylindrical grafts and the tapered grafts were placed in a tissue culture media during processing for cell viability testing. For day three testing, the cylindrical grafts and the tapered grafts were placed in the same tissue culture media with standard tissue culture supplementation and stored at 37° Celsius with $CO_2$ supplementation. For cell viability analysis, the cylindrical and the tapered grafts were sectioned and then assessed for cell viability by fluorescent microscopy using the cell viability stains sytox blue (dead cell stain) and calcein AM (live cell stain). Images of each section of tissue were obtained, and the number of live and dead cells were determined using a validated cell counting protocol. FIG. 7A depicts the cell viability for the cylindrical graft at day zero, and FIG. 7B depicts the cell viability for the tapered graft at day zero. Further, FIG. 7C depicts the cell viability for the cylindrical graft at day three, and FIG. 7D depicts the cell viability for the tapered graft at day three.

Figure 7E:
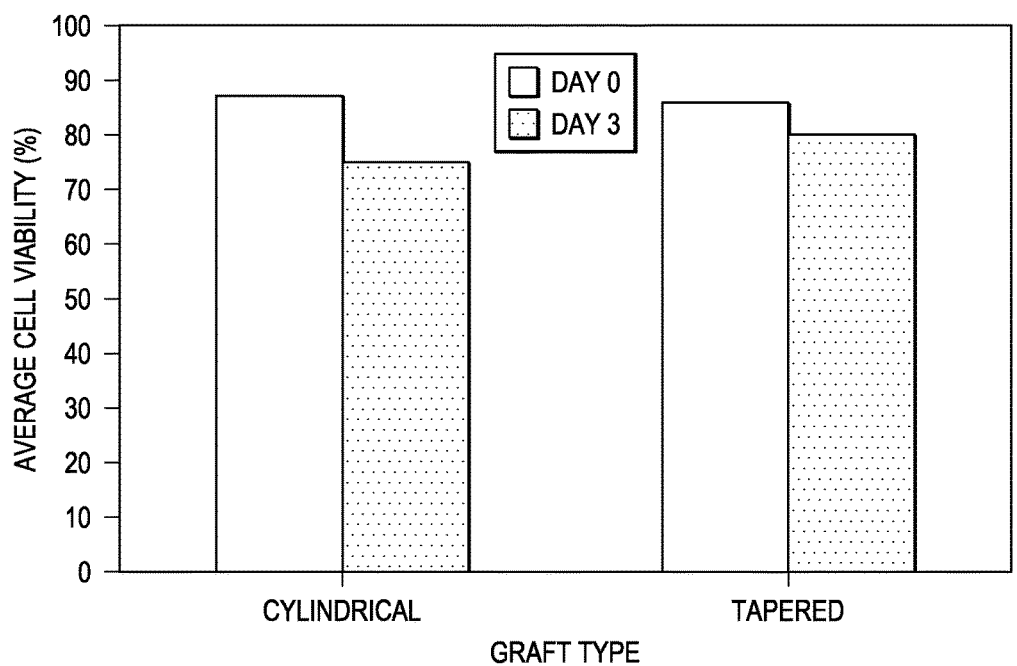

Percent cell viability was calculated by dividing the live cell count by the total cell count and multiplying the result by 100 utilizing the following formula: (live cell count/total cell count)*100. As shown in FIG. 7E, total cell viability did not differ significantly between the tapered and the cylindrical grafts at both day zero and day three after implantation. Such a result indicates that the graft type did not significantly affect total cell viability through day three of culture after graft insertion.

Figure 8A:
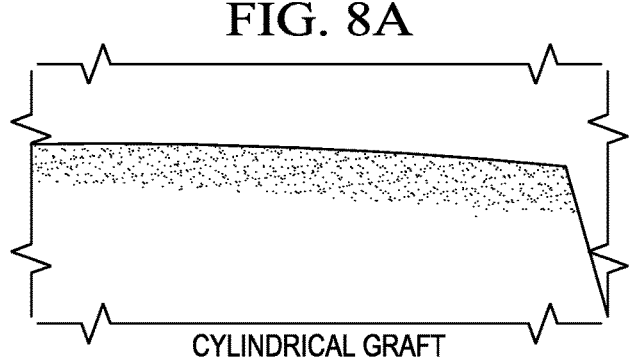
FIGS. 8A-8C illustrate experimental results of cell death for both a prior art cylindrical graft and a tapered graft tissue according to this disclosure.
Figure 8B:
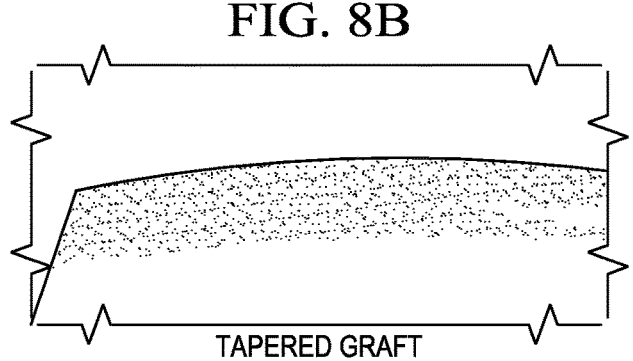
Figure 8C:
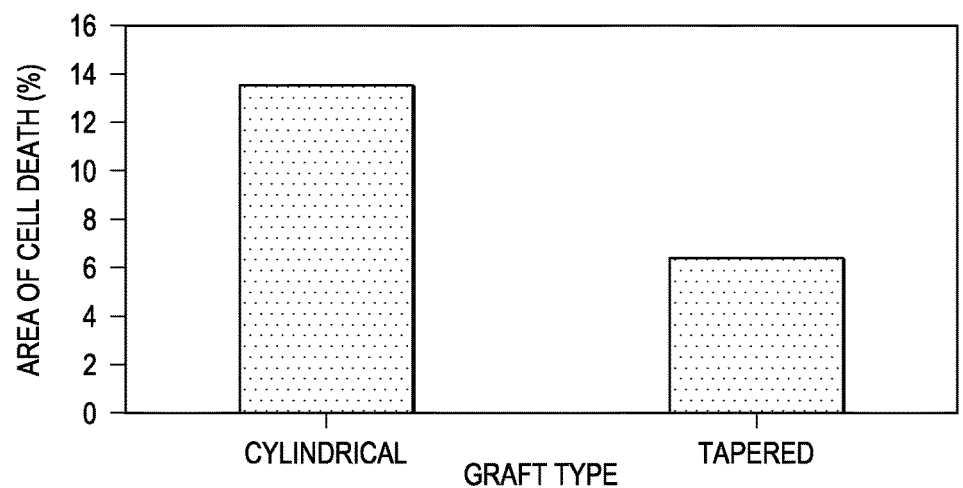

The area of superficial cell death and total tissue area were determined on 4× images. The percent of superficial cell death area was determined by dividing the area of superficial cell death by the total area of the tissue and multiplying the result by 100 utilizing the following formula: (area of superficial cell death/total area of the tissue)*100. The area of superficial cell death is the ratio of the area of low cell viability in the superficial zone compared to the total area of the grafted cartilage tissue. The superficial area of cell death was determined by measuring the area of low cell viability from the superficial surface of the cartilage tissue down to the area of high cell viability deeper in the graft. FIG. 8A depicts the superficial area of cell death for the cylindrical graft, and FIG. 8B depicts the superficial area of cell death for the tapered graft. As shown in FIG. 8C, the tapered grafts had significantly less superficial cell death compared to the cylindrical grafts, suggesting that the tapered graft system is associated with significantly better superficial zone preservation, which may correlate to improved outcomes.

Figure 9A:
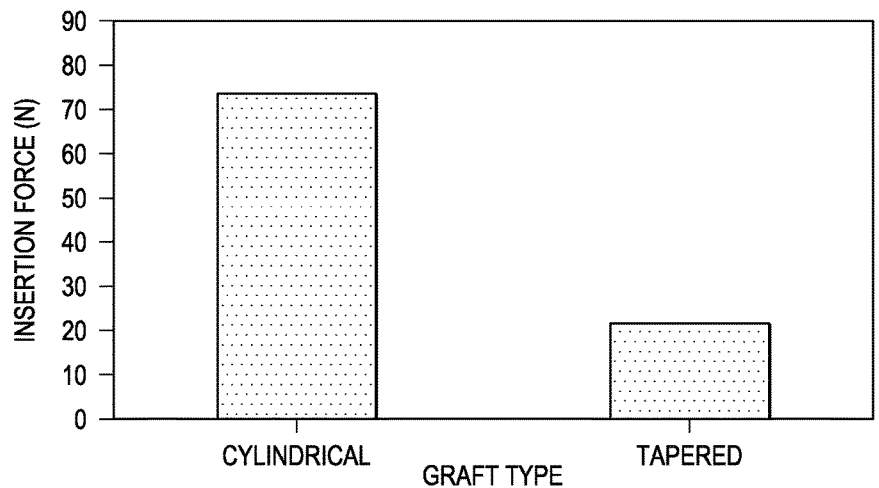
FIGS. 9A-9C illustrate experimental results of insertion force, insertion energy, and extraction force for both a prior art cylindrical graft and a tapered graft tissue according to this disclosure.
Figure 9B:
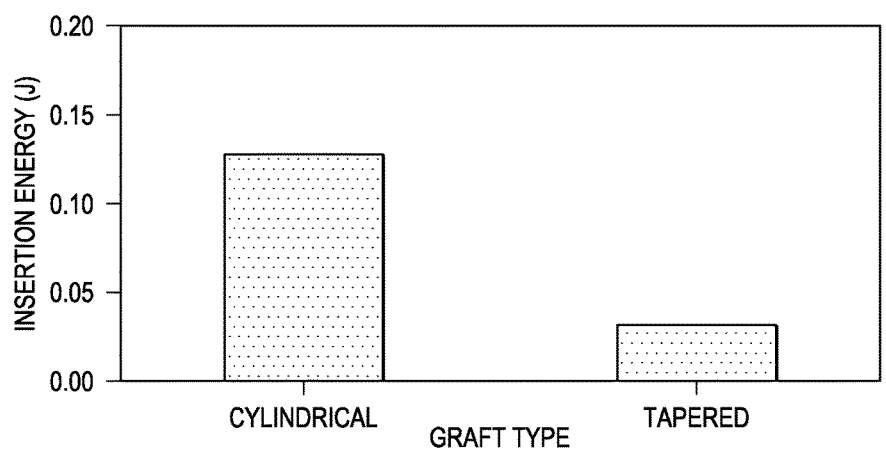

For biomechanical testing, frozen hind limbs from donor test subjects were obtained. Cylindrical grafts were created using a conventional 8 millimeter OCA graft harvester. Tapered grafts were created using a tapered graft system according to this disclosure having an 8 millimeter first diameter cutting surface. The cylindrical grafts and the tapered grafts were trimmed to a depth of 6 millimeters. A 6 millimeter deep cylindrical hole was created for implantation of the cylindrical graft using a conventional cylindrical cannulated reamer. Further, a 6 millimeter deep tapered hole was created for implantation of the tapered graft using a tapered cannulated reamer according to this disclosure. Each graft was manually positioned within the corresponding hole and a servo-hydraulic test machine equipped with a 880N load cell was used to seat each graft at a rate of 0.1 millimeters per second with force and displacement data being collected simultaneously at 100 Hertz. Insertion force was plotted as a function of displacement and the area under this curve was calculated to yield insertion energy for each graft. FIG. 9A depicts the insertion force for both the cylindrical graft and the tapered graft. FIG. 9B depicts the insertion energy for both the cylindrical graft and the tapered graft.

Figure 9C:
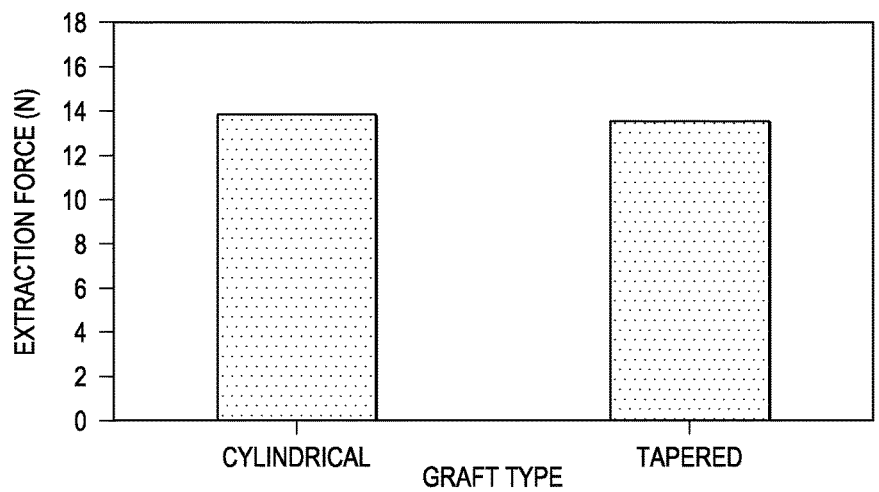

To measure extraction strength, the femur was rotated 180° and a guide pin was placed through the condyle until positioned flush against the opposite side of the graft. The above test machine was utilized to push each graft out, and the extraction strength was calculated for each graft. FIG. 9C depicts the extraction force for both the cylindrical graft and the tapered graft. Statistically significant differences were determined using the students t-test or the rank sum test, depending on data normality, with significance set at $p<0.05$ using Sigma Plot.

As shown in FIGS. 9A-9B, insertion force and energy required to optimally seat the grafts were both significantly lower for the tapered graft system compared to the cylindrical graft system in cadaveric tissues. However, as shown in FIG. 9C, there was not a significant difference between the two graft types for extraction strength required to extract the two types of grafts after insertion. These data indicate that the tapered graft system according to this disclosure may decrease the force and energy required to insert tapered grafts in a clinically relevant manner. Further, the tapered graft system may decrease the associated damage to the tapered graft without compromising stability of the tapered graft after insertion.

Figure 10A:
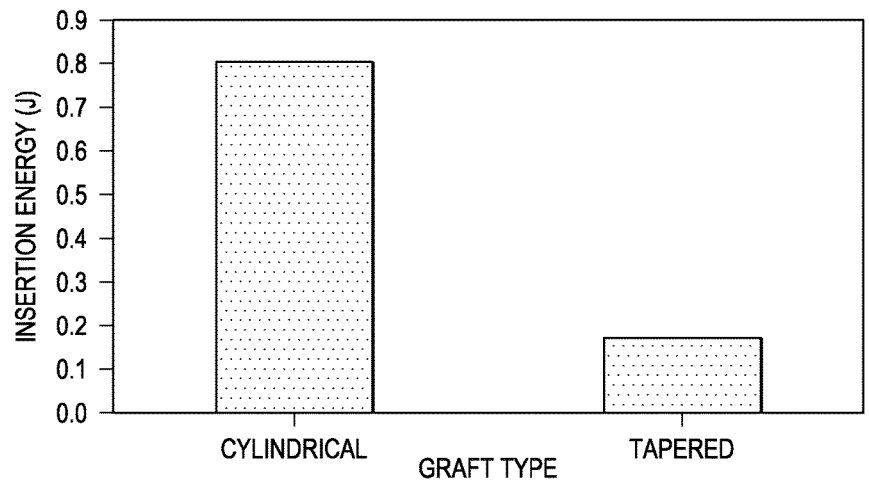
FIGS. 10A-10B illustrate experimental results of insertion energy and extraction force for both a 20 millimeter diameter prior art cylindrical graft and a 20 millimeter diameter tapered graft tissue according to this disclosure.
Figure 10B:
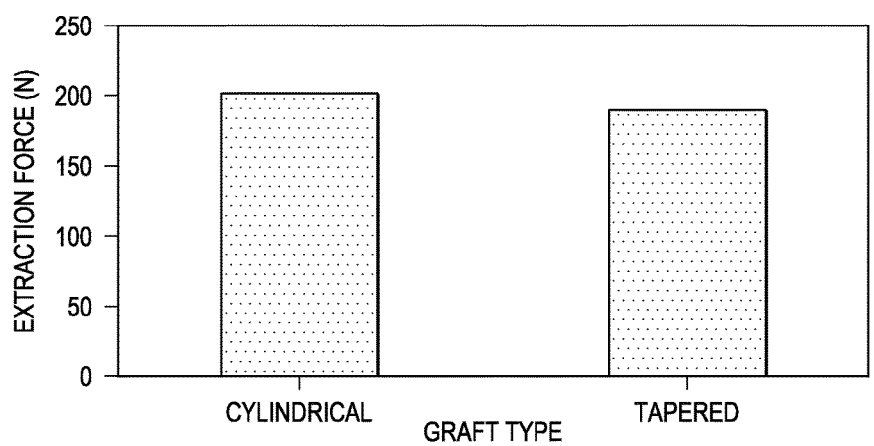

Additional testing was conducted using a tapered graft cutter having a 20 millimeter first diameter cutting surface according to this disclosure to measure insertion energy and extraction force of grafts cut from human femoral condyles. Cadaveric human femoral condyles were acquired from tissue banks. Cylindrical grafts 20 millimeters in diameter and 6 millimeters in height were created and implanted using a conventional cylindrical graft system. Tapered grafts having a 20 millimeter first diameter at a top or exterior facing surface and a 6 millimeter height were created and implanted using a tapered graft system according to this disclosure. Each graft was trimmed to a depth of 6 millimeters prior to being implanted. A 6 millimeter deep cylindrical hole was created for implantation of the cylindrical graft using a conventional cylindrical cannulated reamer. Further, a 6 millimeter deep tapered hole was created for implantation of the tapered graft using a tapered cannulated reamer according to this disclosure. Each graft was manually positioned within the corresponding hole and a servo-hydraulic test machine equipped with a 880N load cell was used to seat each graft. Insertion force was plotted as a function of displacement and the area under this curve was calculated to yield insertion energy for each graft. FIG. 10A depicts the insertion energy for both the cylindrical graft and the tapered graft. Additionally, the above test machine was utilized to push each graft out as described above, and the extraction strength was calculated for each graft. FIG. 10B depicts the extraction force for both the cylindrical graft and the tapered graft. Statistically significant differences were determined using the students t-test or the rank sum test, depending on data normality, with significance set at $p<0.05$ using Sigma Plot.

Similar to the results above, both the insertion force and energy required to optimally seat the tapered grafts were significantly lower compared to the conventional cylindrical grafts in cadaveric tissues. However, there was not a significant difference between the two graft types for extraction strength. Thus, this additional testing indicates that the larger 20 millimeter tapered graft system according to this disclosure may also decrease the force and energy required to insert tapered grafts in a clinically relevant manner. Further, the larger 20 millimeter graft system may decrease the associated damage to the tapered graft without compromising the stability of the tapered graft after insertion.

In summary, the testing shows that the tapered graft system according to this disclosure was associated with significantly lower insertion force and energy required to seat the tapered grafts compared to conventional cylindrical grafts. Further, the tapered grafts exhibited similar extraction strength compared to conventional cylindrical grafts. Thus, the tapered graft system may allow surgeons to implant tapered osteochondral grafts, for example, with much less damage to the grafts while still achieving the desired stability for graft healing and incorporation. Chondrocyte viability assessments from this study support this premise from biomechanical testing in that the tapered grafts were associated with significantly less cell death in the superficial zone of the cartilage. The preservation of superficial zone cartilage in the tapered grafts may be directly related to the lower force and energy required for insertion, and may result in improved clinical outcomes for grafts implanted using the tapered graft system.

While this specification describes a number of non-limiting, illustrative embodiments, various modifications may be made without departing from the scope of this specification as defined by the appended claims. Further, any feature described in connection with any one embodiment may also be applicable to any other embodiment. Thus, this specification contemplates that the various features of the disclosed embodiments may be combined with one another.

What is claimed is:

1. A cutting apparatus, comprising:
   an annular cutting surface adapted to contract from a first diameter to a second diameter that is less than the first diameter to provide a tapered tissue graft;
   the tapered tissue graft having an exposed end and an insertion end separated by a length, the annular cutting surface adapted to automatically contract over the length of the tapered tissue graft from the first diameter at the exposed end to the second diameter at the insertion end, the length between the exposed end and the insertion end defining an external taper of the tapered tissue graft.

2. A cutting apparatus for providing a tapered tissue graft, comprising:
   an annular cutting surface adapted to contract from a first diameter to a second diameter that is less than the first diameter;
   wherein the annular cutting surface is adapted to automatically contract from the first diameter to the second diameter as the annular cutting surface advances into an object.

3. The cutting apparatus of claim 2, wherein the annular cutting surface defines a tapered profile between the first diameter and the second diameter.

4. A cutting apparatus, comprising:
   an elongate housing having a proximal end, a distal end, and a bore defining a longitudinal axis; and
   a plurality of elongate cutting members defining an annular cutting surface at the distal end of the elongate housing, the annular cutting surface adapted to contract from a first diameter to a second diameter that is less than the first diameter to provide a tapered tissue graft having an external taper over a length between the first diameter and the second diameter.

5. The cutting apparatus of claim 4, wherein the first diameter of the annular cutting surface is substantially concentric with the second diameter of the annular cutting surface.

6. A cutting apparatus for providing a tapered tissue graft, comprising:
   an elongate housing having a proximal end, a distal end, and a bore defining a longitudinal axis; and
   a plurality of elongate cutting members defining an annular cutting surface at the distal end of the elongate housing, the annular cutting surface adapted to contract from a first diameter to a second diameter that is less than the first diameter thereby defining a tapered profile between the first diameter and the second diameter;
   further comprising a plunger having an external surface slidably disposed in the bore of the elongate housing, wherein when the annular cutting surface has the first diameter the elongate cutting members are biased against the external surface of the plunger at the distal end of the elongate housing.

7. The cutting apparatus of claim 6, wherein the plunger is slidable toward the proximal end of the elongate housing to permit the annular cutting surface to contract to the second diameter.

8. A system for grafting tissue at a tissue site, comprising:
   an elongate housing having a proximal end, a distal end, and a bore defining a longitudinal axis;
   a plurality of elongate cutting members extending lengthwise at the distal end of the elongate housing and positioned about the longitudinal axis of the elongate housing, the elongate cutting members defining an annular cutting surface adapted to contract from a first diameter to a second diameter that is less than the first diameter thereby defining a tapered profile between the first diameter and the second diameter; and
   a plunger having an external surface slidably disposed in the bore of the elongate housing, wherein when the annular cutting surface has the first diameter the elongate cutting members are biased against the external surface of the plunger at the distal end of the elongate housing.

9. The system of claim 8, further comprising a reamer having an external cutting surface, a proximal end, and a distal end, the external cutting surface of the reamer having a first diameter at the proximal end of the reamer and a second diameter at the distal end of the reamer, the reamer defining a tapered profile between the first diameter of the reamer and the second diameter of the reamer that substantially corresponds to the tapered profile between the first diameter of the annular cutting surface and the second diameter of the annular cutting surface.

10. The system of claim 9, wherein the reamer has a bore substantially aligned along a length and about an axis of the reamer, the bore of the reamer being adapted to receive a reamer guide pin.

11. The system of claim 8, wherein the bore of the elongate housing has a substantially constant internal diameter along a length of the elongate housing.

12. The system of claim 8, further comprising an arbor positioned at the proximal end of the elongate housing and substantially aligned with the longitudinal axis of the elongate housing, the arbor being adapted to couple the elongate housing to a surgical drill.

13. The system of claim 12, further comprising a plunger guide rod adapted to extend from the plunger along the longitudinal axis of the elongate housing, the arbor having an aperture adapted to receive an end of the plunger guide rod.

14. The system of claim 8, wherein the first diameter of the annular cutting surface is substantially concentric with the second diameter of the annular cutting surface.

15. The system of claim 8, wherein the plunger is slidable toward the proximal end of the elongate housing to permit the annular cutting surface to contract to the second diameter.

16. The system of claim 8, further comprising a plunger guide rod adapted to extend from the plunger along the longitudinal axis of the elongate housing.

* * * * *